(12) United States Patent
Mitchell

(10) Patent No.: US 8,066,760 B2
(45) Date of Patent: Nov. 29, 2011

(54) STENT WITH MOVABLE CROWN

(75) Inventor: James Mitchell, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 418 days.

(21) Appl. No.: 11/379,161

(22) Filed: Apr. 18, 2006

(65) Prior Publication Data

US 2007/0244543 A1 Oct. 18, 2007

(51) Int. Cl.
*A61F 2/06* (2006.01)

(52) U.S. Cl. ............................. 623/1.15; 623/1.11

(58) Field of Classification Search ................ 623/1.15, 623/1.16, 1.17, 1.2, 1.12, 1.11, 1.13, 1.14, 623/1.25, 1.32, 1.35, 1.36, 1.38
See application file for complete search history.

(56) References Cited

U.S. PATENT DOCUMENTS

| | | | | |
|---|---|---|---|---|
| 5,441,515 A | * | 8/1995 | Khosravi et al. | 606/194 |
| 5,776,181 A | * | 7/1998 | Lee et al. | 623/1.15 |
| 6,019,789 A | * | 2/2000 | Dinh et al. | 623/1.15 |
| 6,027,527 A | * | 2/2000 | Asano et al. | 623/1.15 |
| 6,231,598 B1 | * | 5/2001 | Berry et al. | 623/1.15 |
| 6,293,967 B1 | * | 9/2001 | Shanley | 623/1.15 |
| 6,295,714 B1 | * | 10/2001 | Roychowdhury et al. | 29/516 |
| 6,773,455 B2 | * | 8/2004 | Allen et al. | 623/1.15 |
| 7,291,166 B2 | * | 11/2007 | Cheng et al. | 623/1.15 |
| 2003/0199970 A1 | * | 10/2003 | Shanley | 623/1.16 |
| 2004/0102837 A1 | * | 5/2004 | Boyle et al. | 623/1.16 |
| 2005/0149111 A1 | * | 7/2005 | Kanazawa et al. | 606/200 |
| 2005/0182474 A1 | | 8/2005 | Jones et al. | |

FOREIGN PATENT DOCUMENTS

| | | |
|---|---|---|
| EP | 1645300 | 4/2006 |
| WO | WO2006/005027 | 1/2006 |

* cited by examiner

*Primary Examiner* — S. Thomas Hughes
*Assistant Examiner* — Jocelin Tanner

(57) ABSTRACT

A system for treating abnormalities of the cardiovascular system includes a stent having a plurality of movable crown portions. When the stent is expanded, the crown portions move to a diameter recoil prevention position. One embodiment of the invention includes crown portions that translate from a concave to a convex configuration with respect to the strut portions of the stent during expansion of the stent. Another embodiment of the invention includes a method reducing diameter recoil of stent upon expansion of the stent.

12 Claims, 6 Drawing Sheets

STENT WITH MOVABLE CROWN

TECHNICAL FIELD

This invention relates generally to biomedical devices that are used for treating vascular conditions. More specifically, the invention relates to a stent that includes a movable crown portion that reduces diameter recoil upon expansion of the stent.

BACKGROUND OF THE INVENTION

Stents are generally cylindrical-shaped devices that are radially expandable to hold open a segment of a vessel or other anatomical lumen after implantation into the body lumen.

Various types of stents are in use, including expandable and self-expanding stents. Expandable stents generally are conveyed to the area to be treated on balloon catheters or other expandable devices. For insertion into the body, the stent is positioned in a compressed configuration on the delivery device. For example, the stent may be crimped onto a balloon that is folded or otherwise wrapped about the distal portion of a catheter body that is part of the delivery device. After the stent is positioned across the lesion, it is expanded by the delivery device, causing the diameter of the stent to expand. For a self-expanding stent, commonly a sheath is retracted, allowing the stent to expand.

Stents are used in conjunction with balloon catheters in a variety of medical therapeutic applications, including intravascular angioplasty. For example, a balloon catheter device is inflated during percutaneous transluminal coronary angioplasty (PTCA) to dilate a stenotic blood vessel. The stenosis may be the result of a lesion such as a plaque or thrombus. When inflated, the pressurized balloon exerts a compressive force on the lesion, thereby increasing The inner diameter of the affected vessel. The increased interior vessel diameter facilitates improved blood flow. Soon after the procedure, however, a significant proportion of treated vessels restenose.

To prevent restenosis, stents, constructed of metals or polymers, are implanted within the vessel to maintain lumen size. The stent is sufficiently longitudinally flexible so that it can be transported through the cardiovascular system. In addition, the stent requires sufficient radial strength to act as a scaffold and support the lumen wall in a circular, open configuration. Configurations of stents include a helical coil, and a cylindrical sleeve defined by a mesh, which may be supported by struts or a series of rings fastened together by struts.

Stent insertion may cause undesirable reactions such as inflammation resulting from a foreign body reaction, infection, thrombosis, and proliferation of cell growth that occludes the passageway. Stents with polymer coatings have been used to deliver drugs or other therapeutic agents at the site of the stent that may assist in preventing these conditions. Another approach to this problem is to use biodegradable stents composed of polymers that, over a defined period of time, are removed from the body. Such temporary implants remain in place during healing at the treatment site, but then disappear, thereby minimizing many of the deleterious effects of long term implants such as inflammation, cellular proliferation and thrombosis.

Another parameter to be considered in stent design is diameter recoil, the tendency of the stent to revert toward its compressed diameter following expansion. Diameter recoil or constriction is due primarily to the elastic properties of the material comprising the stent, and is generally greater for polymeric stents than for those comprising metals such as stainless steel. Diameter recoil may cause the stent to partially block blood flow through the vessel, or to become dislodged from the treatment site.

It would be desirable, therefore, to provide an implantable polymeric stent that retains the longitudinal flexibility needed for efficient delivery and the radial strength to support the vessel wall, but also exhibits minimal diameter recoil upon expansion of the stent, and may additionally be biodegradable. Such a stent would overcome many of the limitations and disadvantages inherent in the devices described above.

SUMMARY OF THE INVENTION

One aspect of the present invention provides a system for treating abnormalities of the cardiovascular system comprising a catheter and a stent disposed on the catheter. The stent includes a plurality of flexible crown portions. When the stent is radially expanded at the treatment site, the crown portions move to a diameter recoil prevention position, and thus prevent diameter recoil of the stent.

Another aspect of the invention provides a polymeric stent comprising a plurality of elongated strut portions and a plurality of flexible crown portions extending from the strut portions. When the stent is radially expanded the flexible crown portions assume a diameter recoil prevention position.

Another aspect of the invention provides a method for treating a vascular condition. The method comprises delivering a stent including a plurality of crown portions to a treatment site using a catheter. The method further comprises radially expanding the stent at the treatment site, and moving the crown members to a diameter recoil prevention position in response to the expansion of the stent.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

Throughout this specification, like numbers refer to like structures.

Figure 1A:
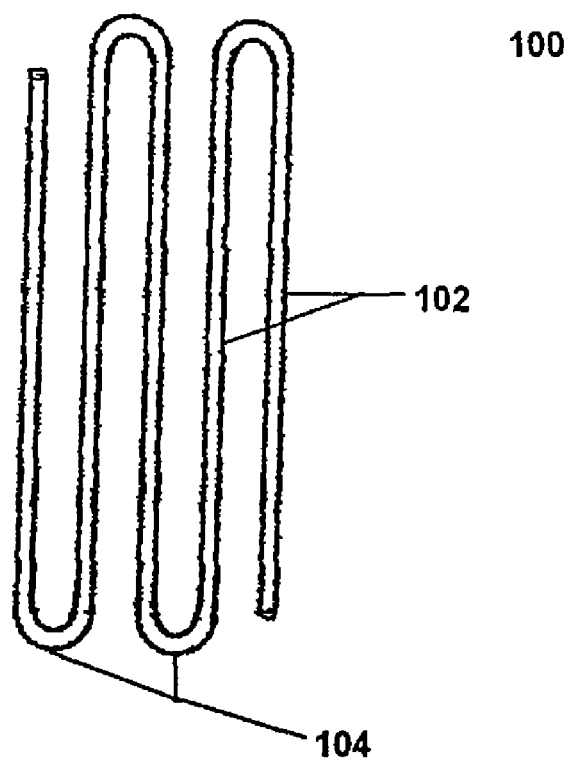
FIG. 1A is a schematic illustration of a portion of a stent in a contracted configuration.

Referring to the drawings, FIG. 1 is a schematic representation of a portion of a stent 100 when the stent is in a compressed configuration. The structure comprises a series of elongated strut portions 102 and curved crown portions 104 longitudinally adjoining strut portions 102. To form stent 200, shown in FIGS. 2A and 2B, the flat planar configuration of stent 100 shown in FIG. 1A, is formed into the cylindrical or tubular structure shown in FIG. 2A. Strut portions 102 provide radial strength, enabling stent 200 to maintain vessel patency.

Figure 1B:
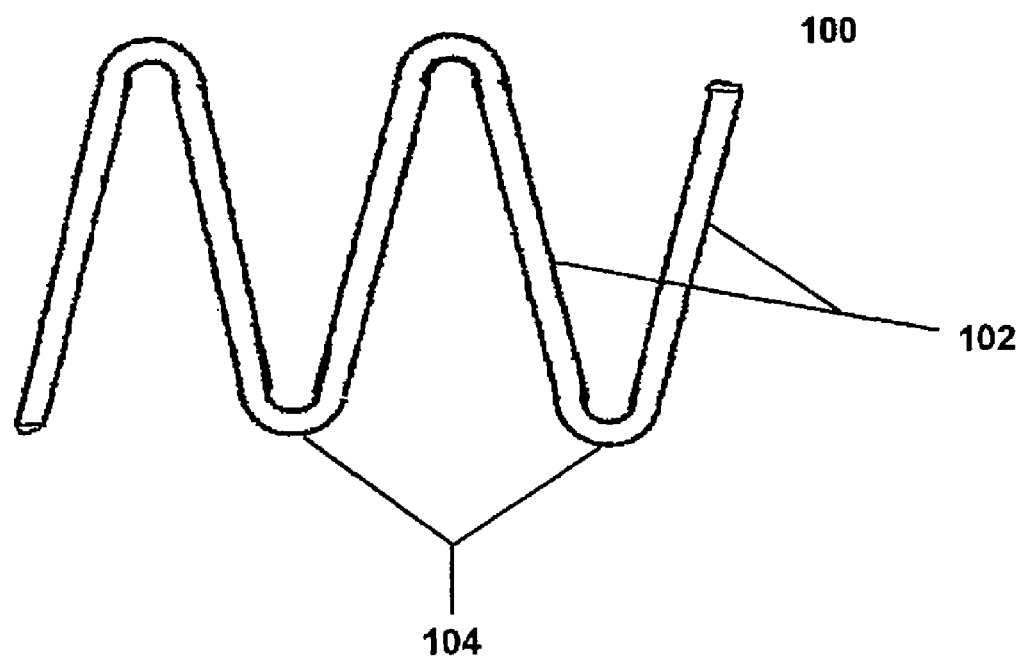
FIG. 1B is a schematic illustration of a portion of a stent in an expanded configuration.
Figures 2A, 2B:
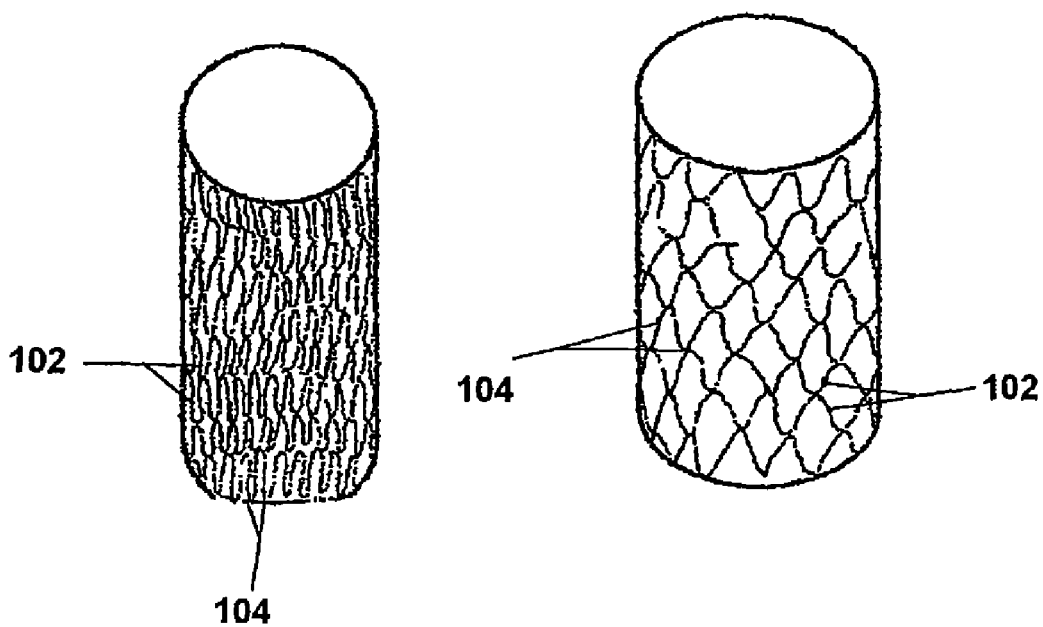
FIG. 2A is an exterior view of the cylindrical stent when the stent is compressed.
FIG. 2B is an exterior view of the cylindrical stent when the stent is expanded.

Vascular stents are frequently mounted on a delivery catheter in a compressed configuration as shown in FIGS. 1A and 2A, and transported through the vascular system to the site of the vascular lesion requiring treatment. Once at the treatment site, stent 200 is deployed from the catheter by radially expanding stent 200, and lodging stent 200 firmly against the interior surface of the vascular wall. Stent portion 100 is shown in an expanded configuration in FIGS. 1B and 2B. As shown in FIG. 1B, strut portions 102 move laterally away from each other as the diameter of stent 200 increases (FIG. 2B). Stent 200 may be self expanding or balloon expandable, depending on both the dimensions of stent 100 and the material comprising stent 100.

Metallic stents comprise a variety of biocompatible metals including stainless steel, titanium, gold, nickel/titanium alloys, such as nitinol, platinum, and platinum-tungsten alloys. These metallic materials are sufficiently flexible to allow the stent to be compressed and expanded, but also provide sufficient radial strength to maintain the stent in the expanded configuration and apply adequate force to the vessel wall to hold the stent in place and maintain vessel patency. Such stents are, however, permanent implants, and sometimes cause a foreign body reaction resulting in inflammation and cellular proliferation.

In one embodiment of the invention, stent 100 comprises one or more biocompatible polymeric materials. Polymeric stents may be biodegradable, biostable, or comprise a mixture of polymeric materials that are both biostable and biodegradable. Biodegradable polymers appropriate for the stents of the invention include polylactic acid, polyglycolic acid, and their copolymers, caproic acid, polyethylene glycol, polyanhydrides, polyacetates, polycaprolactones, poly(orthoesters), polyamides, polyurethanes and other suitable polymers. Biostable polymers appropriate for the stents of the invention include polyethylene, polypropylene, polymethyl methacrylate, polyesters, polyamides, polyurethanes, polytetrafluoroethylene (PTFE), polyvinyl alcohol, and other suitable polymers. These polymers may be used alone or in various combinations to give the stent unique properties such as controlled rates of degradation, or to form biostable stents with a biodegradable or bioerodable coating that may reduce inflammation, control tissue ingrowth, and additionally, release a drug.

In addition to the above properties, the stent material must be able to withstand the strain that is placed on the stent during expansion. Strain is a measure of the displacement that can be applied to a material before the material breaks or tears. Strain is measured as the ratio of the change in length of the material to the original length of the material.

Figure 3:
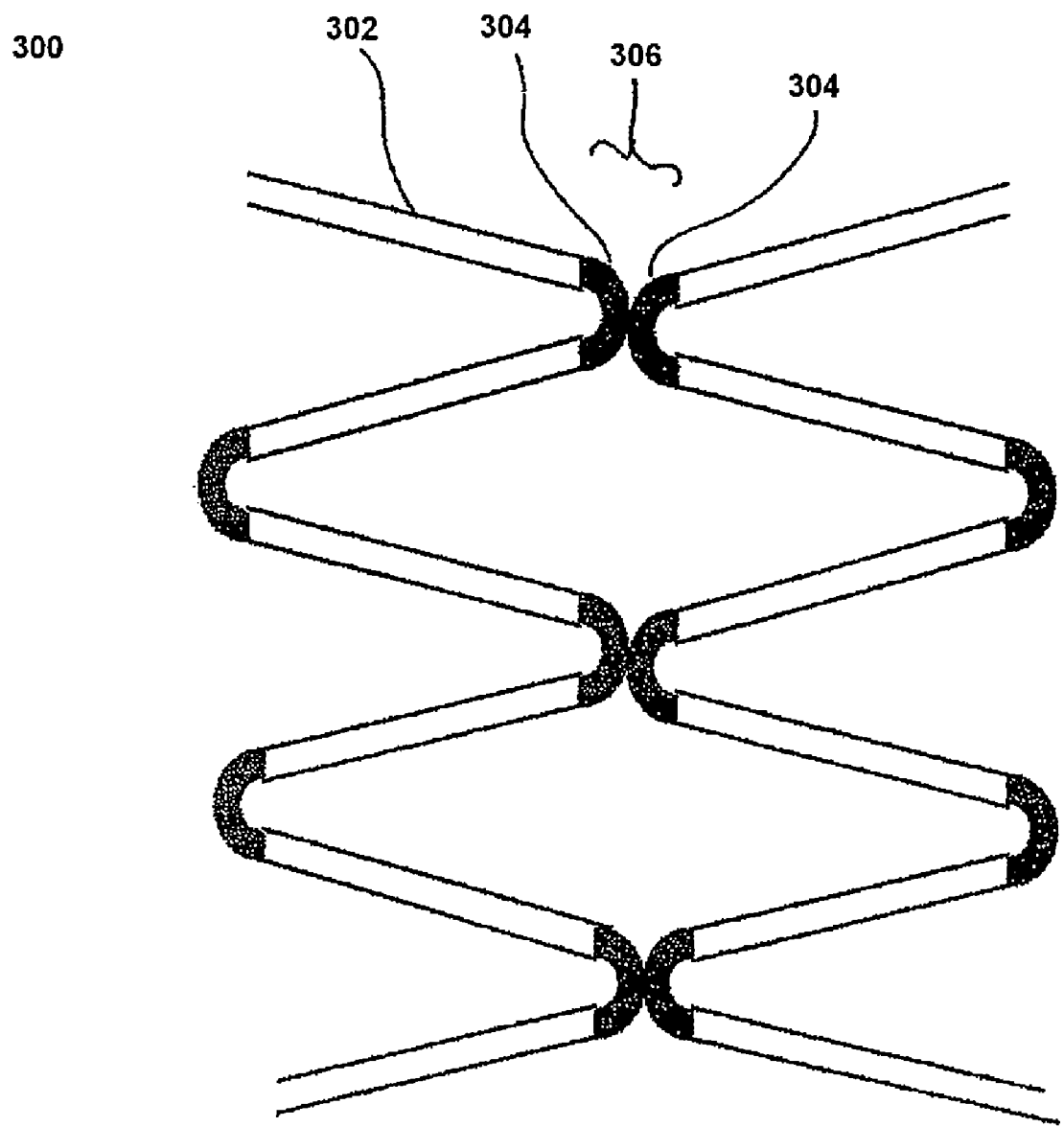
FIG. 3 is a schematic illustration of the stent portion shown in FIG. 1B indicating regions of the stent undergoing increased strain due to radial expansion of the stent, in accordance with the present invention.

Despite the advantages stents comprising polymeric materials offer, they also have drawbacks. One of the undesirable characteristics of polymeric stents is diameter recoil. Diameter recoil is the tendency of stent 200, after it has been expanded, to partially revert from its expanded configuration (FIG. 2B) toward its compressed configuration, shown in FIG. 2A. In one embodiment of the invention, diameter recoil is reduced by constructing stent 300 from polymeric materials that decrease in flexibility when placed under strain. Examples of polymers having this characteristic, known as strain hardening, include polyethylene and polypropylene. When such stents 300 are expanded and strut portions 302 move away from each other, crown portions 304 act as hinges, causing the angles formed by crown portions 304 to increase. The bending of crown portions 304 to a wider angle places crown portions 304 under strain. FIG. 3 shows crown portions 304 in a strained configuration, and portions 306 of stent 300 that are strained. In one embodiment of the invention, the polymeric materials comprising stent 300 are capable of withstanding strain of, for example, 0.4 or greater. In response to strain, portions 306 become strain hardened, and form less flexible bands along the length of stent 300. Diameter recoil is reduced due to the relative inflexibility of strain hardened portions 306 of the of stent 300.

Figure 4:
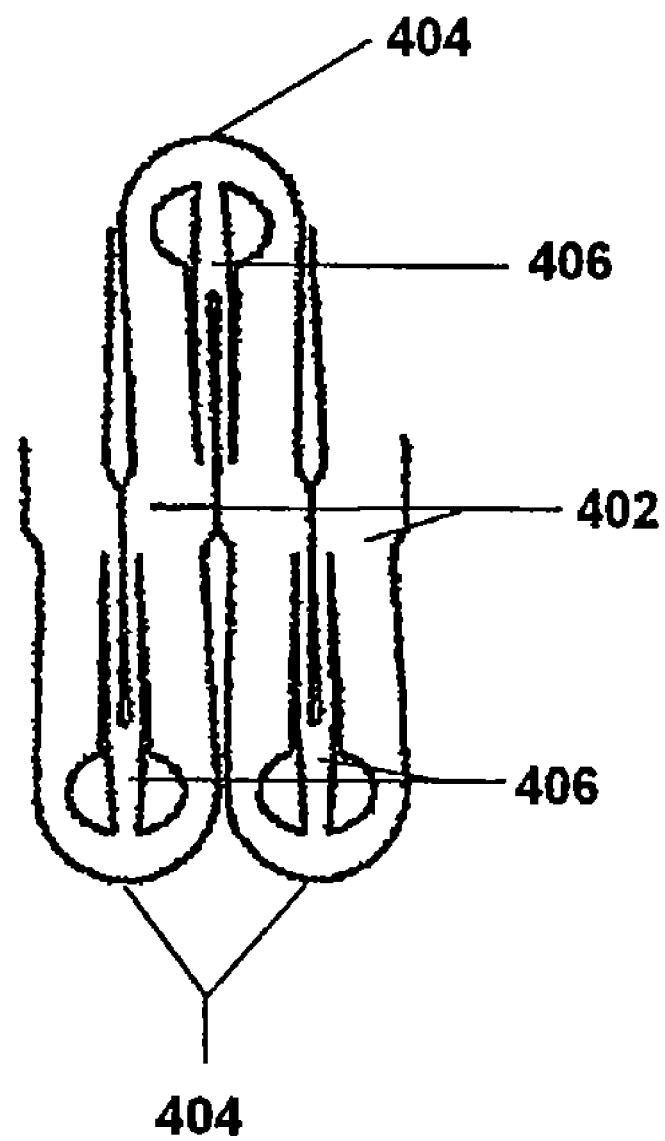
FIG. 4 is a schematic illustration of strut portions and movable crown portions of a stent in a compressed configuration, in accordance with the present invention.

FIG. 4 is a schematic illustration of a portion of stent 400 in a compressed configuration, in accordance with the present invention. Stent 400 comprises a polymeric material, and elongated strut portions 402 are attached to movable crown portions 404. As can be seen in FIG. 4, crown portions 404 are concave with respect to strut portions 402 in the compressed configuration. In addition, the stent includes movable connector portions 406 attached to both strut portions 402 and crown portions 404. Each connector portion 406 is attached at its distal end to a crown portion 404. The proximal end of each connector portion 406 is bifurcated, and is attached to two adjacent strut portions.

Figure 5A:
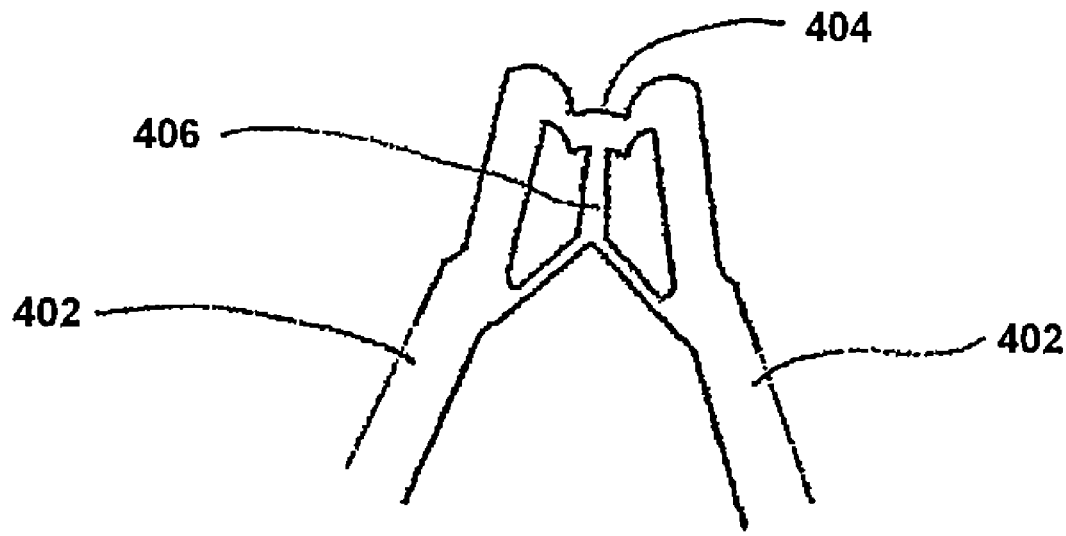
FIG. 5A is a schematic illustration of one embodiment of a movable crown portion of a stent connected to movable connectors, in accordance with the present invention.

As shown in FIG. 5A, when stent wall 400 is expanded and strut portions 402 move laterally away from each other, the bifurcated proximal end of connector portion 406 opens and effectively shortens connector portion 406. This shortening of connector portion 406 in turn draws attached crown portion 404 longitudinally along the length of the stent toward strut portions 402. As crown portion 404 is drawn toward strut portions 402, crown portion 404 assumes a recoil prevention position. In this recoil prevention position, the longitudinal movement of the crown portion 404 adds an additional recoil direction for the crown. The longitudinal recoil direction reduces the diameter recoil of the stent in the expanded configuration of the stent.

Figure 5B:
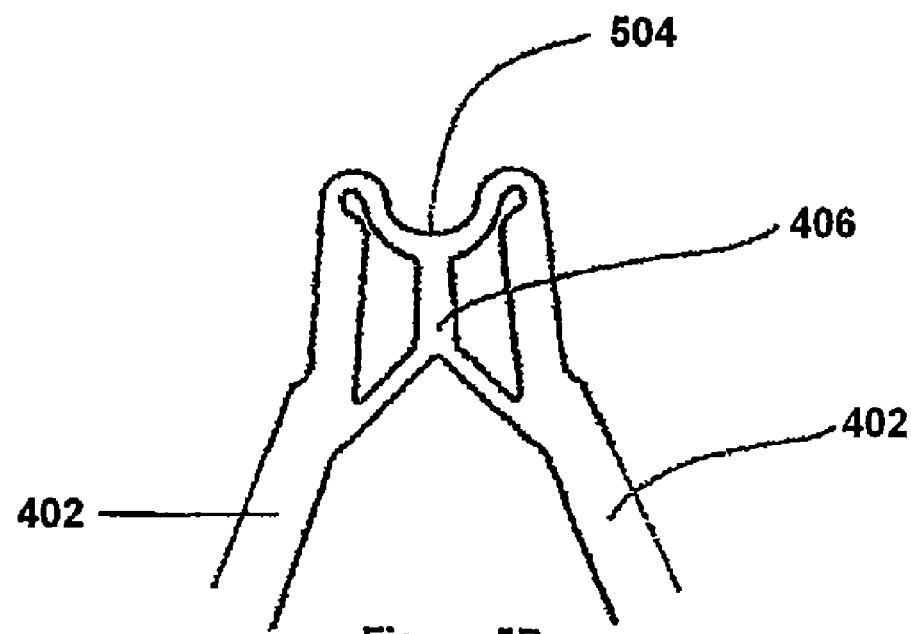
FIG. 5B is a schematic illustration of an embodiment of a movable crown portion of a stent connected to movable connectors in which the crown changes shape in response to expansion of the stent, in accordance with the present invention.

Another embodiment of the invention, movable crown 504, is shown schematically in FIG. 5B. Crown portion 504 is attached to strut portions 402 and movable connector portions 406. As the stent expands and strut portions 402 move laterally away from each other, connector portion 406 shortens and draws crown portion 504 toward strut portions 402. As crown portion 504 is drawn longitudinally toward strut portions 402, crown portion 504 translates from a concave configuration to a convex configuration with respect to strut portions 402. The convex configuration of crown portion 504 is a recoil prevention position that reduces diameter recoil of the expanded stent. In addition, a stent having either crown portion 404 or 504 may comprise a polymeric material that undergoes strain hardening. Expansion of the stent causes strain at the interface between strut portions 402 and either crown portion 404 or 504 resulting in strain hardening and a further reduction of diameter recoil of the stent.

Figure 6:
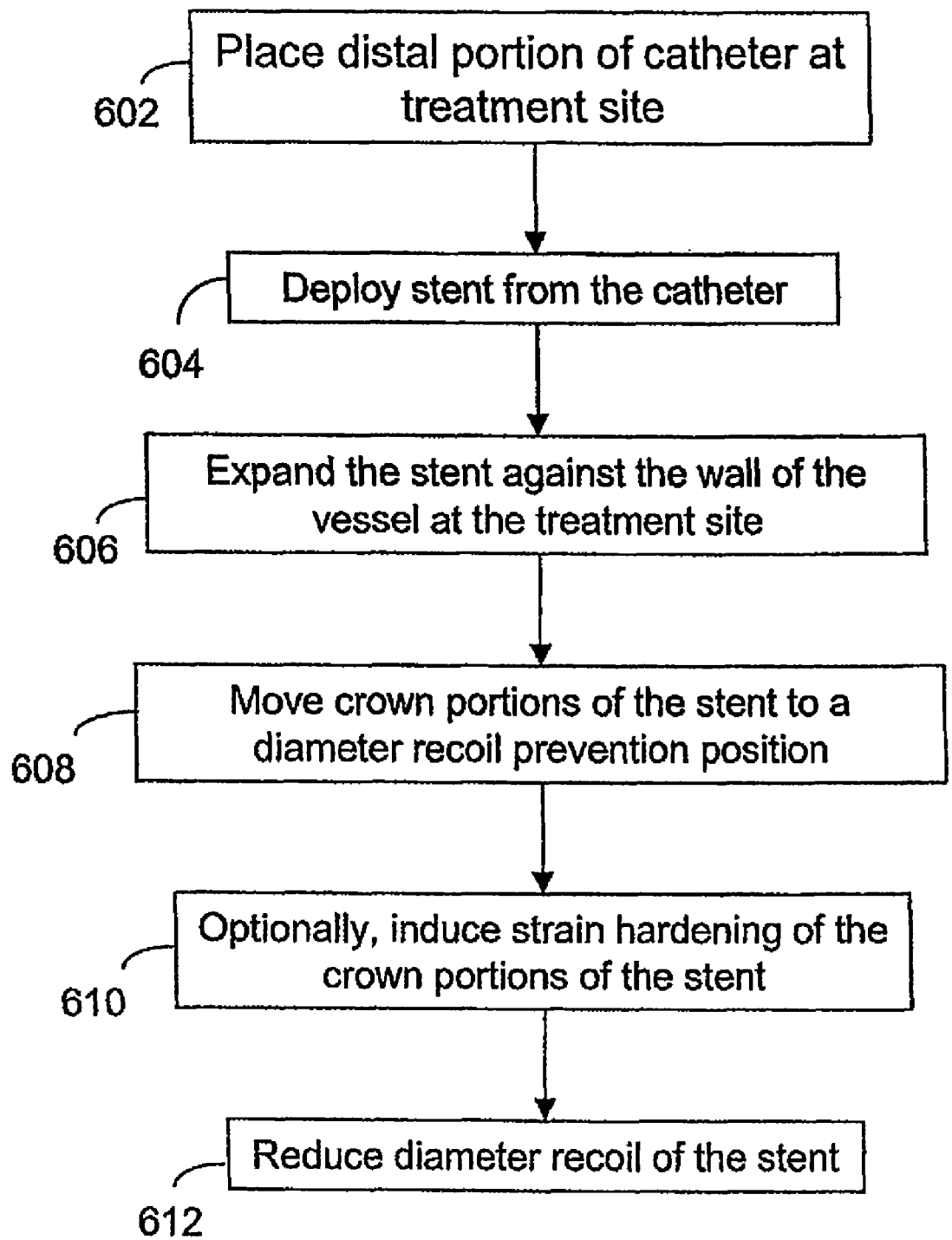
FIG. 6 is a flow diagram of a method of treating a vascular condition using a stent with movable crown portions, in accordance with the present invention.

FIG. 6 is a flowchart of method 600 for treating vascular abnormalities using a stent. The method includes selecting a stent comprising a polymeric material, and delivering the stent to the treatment site using a delivery catheter, as shown in Block 602. The stent is mounted on the delivery catheter in a compressed configuration on a balloon. Next, the distal portion of the delivery catheter is inserted into the vascular system of the patient, and advanced through the vascular system to the treatment site.

When the stent is positioned across the vascular lesion to be treated, the stent is deployed from the catheter, as indicated in Block 604. As the stent is deployed from the catheter, it is expanded (Block 606), causing the diameter of the stent to increase, pressing the exterior surface of the stent against the interior surface of the vascular wall, and lodging the stent firmly in place. As the stent is expanded, the crown portions of the stent move to a diameter recoil prevention position, as indicated in Block 608. During expansion of the stent, the strut portions move laterally away from each other. The movable connector portions, longitudinally connected to both the strut portions and the crown portions of the stent, draw the crown portions toward the strut portions. The movable bifurcated connector portions attached to the strut portions and the crown portions deform based on the expansion of the stent, as illustrated in FIGS. 5A and 5B. In one embodiment of the invention, the crown portions of the stent translate from a concave to a convex configuration in relation to the strut portions.

Optionally, as indicated in Block 610, depending on the physical characteristics of the polymeric material comprising the stent, the crown portions of the stent may undergo strain hardening as a result of the expansion of the stent. In any case, the crown portions of the stent move to a diameter recoil prevention position and reduce diameter recoil of the stent (Block 612) in response to the expansion of the stent. Diameter recoil may be further reduced if the crown portions of the stent are subject to strain hardening in the expanded configuration.

While the invention has been described with reference to particular embodiments, it will be understood by one skilled in the art that variations and modifications may be made in form and detail without departing from the spirit and scope of the invention.

The invention claimed is:

1. A system for treating a vascular condition comprising;
a catheter;
a stent disposed on the catheter, the stent including a plurality of flexible crown portions, elongated longitudinal strut portions extending from the crown portions, and movable bifurcated connector portions having a first end attached to the crown portion and bifurcated portion ends attached to the elongated longitudinal strut portions extending from the crown portion;
wherein the crown portions are configured to move from a compressed configuration to a diameter recoil prevention configuration when the stent is expanded,
wherein the crown portions are concave with respect to the strut portions in the compressed configuration and convex with respect to the strut portions in the expanded diameter recoil prevention configuration, and
wherein when the stent is expanded the elongated longitudinal strut portions move laterally apart and the first end of the movable bifurcated connector portion draws the crown portion longitudinally into the diameter recoil prevention position.

2. The stent of claim 1 wherein the stent comprises a polymer or combination of polymers capable of withstanding strain of 0.4 or greater.

3. The stent of claim 1 wherein the crown members comprise a polymer or combination of polymers that strain harden when the crown portions undergo a shape change.

4. The stent of claim 1 wherein the stent comprises one or more biostable or biodegradable polymers.

5. The stent of claim 4 wherein the stent comprises one or more biodegradable polymeric materials selected from the group consisting of polylactic acid, polyglycolic acid, and their copolymers, polyamides polyurethanes and other suitable polymers.

6. The expandable stent of claim 4 wherein the stent comprises one or more biostable polymeric materials selected from the group consisting of polyethylene, polypropylene, polymethyl methacrylate, polyesters, polyamides, polyurethanes, polytetrafluoroethylene, polyvinyl alcohol, and other suitable polymers.

7. A polymeric stent comprising:
a plurality of flexible crown portions, the crown portions configured to move from a compressed configuration to a diameter recoil prevention configuration when the stent is expanded;
a plurality of elongated longitudinal strut portions extending from the crown portions; and
a plurality of movable bifurcated connector portions, wherein each of the bifurcated connector portions comprise an elongated portion having a first end attached to a crown portion and a bifurcated portion having a first bifurcated end attached to a first strut portion and a second bifurcated end attached to a second strut portion, the bifurcated connector portions further comprising a length selected to deform the crown portion when an angle between the longitudinal struts is increased separating the bifurcated ends and moving the flexible crown portions from the compressed configuration into the diameter recoil prevention position, wherein the crown portions are concave with respect to the strut portions in the compressed configuration and convex with respect to the strut portions in the expanded diameter recoil prevention configuration.

8. The stent of claim 7 wherein the crown portions strain harden during expansion of the stent and thereby reduce the diameter recoil of the stent.

9. The stent of claim 7 wherein the stent comprises a polymer or combination of polymers capable of withstanding strain of 0.4 or greater.

10. A method of treating a vascular condition comprising:
delivering a stent including a plurality of crown portions and a plurality of longitudinal strut portions extending from the crown portions to a treatment site via catheter;
expanding the stent at the treatment site;
deforming movable bifurcated connector portions directly attached to the strut portions and the crown portions based on the expansion of the stent; and
moving the crown portions to a diameter recoil prevention position based on the deformation of the crown portions, wherein the crown portions are moved from a concave compressed configuration with respect to the strut portions to a convex configuration in the diameter recoil prevention position.

11. The method of claim 10 further comprising selecting a stent polymeric material capable of withstanding strain of 0.4 or greater.

12. The method of claim 11 further comprising selecting a stent polymeric material that undergoes strain hardening upon expansion of the stent.

* * * * *